US006235793B1

(12) United States Patent
Bernat et al.

(10) Patent No.: US 6,235,793 B1
(45) Date of Patent: May 22, 2001

(54) USE OF AGONISTS OF ADRENERGIC β-3 RECEPTORS FOR PREPARING WOUND-HEALING MEDICINES

(75) Inventors: André Bernat, Cugnaux; Jean-Marc Herbert, Tournefeuille; Michèle Arnone, Ramonville St Agne, all of (FR)

(73) Assignee: Sanofi-Synthelabo, Paris (FR)

( * ) Notice: Subject to any disclaimer, the term of this patent is extended or adjusted under 35 U.S.C. 154(b) by 0 days.

(21) Appl. No.: 09/341,656
(22) PCT Filed: Jan. 21, 1998
(86) PCT No.: PCT/FR98/00105
  § 371 Date: Jul. 15, 1999
  § 102(e) Date: Jul. 15, 1999
(87) PCT Pub. No.: WO98/31357
  PCT Pub. Date: Jul. 23, 1998

(30) Foreign Application Priority Data

Jan. 21, 1997 (FR) .................................................. 97 00584

(51) Int. Cl.$^7$ .................................................. A61K 31/135
(52) U.S. Cl. ............................. 514/652; 514/646; 514/653
(58) Field of Search ..................... 514/463, 376, 514/450, 451, 327, 640, 652, 653; 424/319, 309, 276, 78.05; 530/306

(56) References Cited

U.S. PATENT DOCUMENTS

| 4,341,793 | * | 7/1982 | Ferris | 514/469 |
| 5,153,210 | * | 10/1992 | Ainsworth et al. | 514/369 |
| 5,502,078 |   | 3/1996 | Holloway et al. . | |
| 5,512,592 | * | 4/1996 | Zaloga et al. | 514/400 |
| 5,578,638 | * | 11/1996 | Brazzell et al. | 514/463 |
| 5,585,396 | * | 12/1996 | Zaloga et al. | 514/400 |
| 5,597,797 | * | 1/1997 | Clark | 514/12 |
| 5,597,843 |   | 1/1997 | Girten et al. . | |
| 5,869,450 | * | 2/1999 | Wei et al. | 514/12 |
| 5,962,477 | * | 10/1999 | Mak | 514/327 |

FOREIGN PATENT DOCUMENTS

WO94/24090   10/1994   (WO) .

OTHER PUBLICATIONS

K. Kuratani et al., "Enhancement of Gastric Mucosal Blood Flow by β–3 Adrenergic Agonists Prevents Indomethacin–Induced Antral Ulcer in the Rat", *J. Pharmacol. Exp. Ther.*, 270 (2), 1994, pp. 559–565.

Y.–T. Shen et al., "Peripheral Vascular Effects of β–3 Adrenergic Receptor Stimulation in Conscious Dogs", *J. Pharmacol. Exp. Ther.*, 268 (1), 1994, pp. 466–473.

Derwent Abstract No. AN 95–332486 (JP 07228543A), 1995.

JRS Arch et al., "Prospects for β3–Adrenoreceptor Agonists in the Treatment of Obesity and Diabetes", *Int. J. Obesity*, 20 (3), 1996, pp. 191–199.

* cited by examiner

*Primary Examiner*—William R. A. Jarvis
*Assistant Examiner*—Vickie Kim
(74) *Attorney, Agent, or Firm*—Michael D. Alexander; Paul E. Dupont

(57) ABSTRACT

The invention relates to the use of $β_3$-adrenergic receptor agonists for the preparation of healing drugs and to the pharmaceutical compositions for said use.

8 Claims, No Drawings

USE OF AGONISTS OF ADRENERGIC β-3 RECEPTORS FOR PREPARING WOUND-HEALING MEDICINES

This application is a 371 of PCT/FR98/00105 filed Jan. 21, 1998.

The present invention relates to a novel indication of β₃-adrenergic receptor agonists.

More particularly, the invention relates to the use of β₃-adrenergic receptor agonists for the preparation of wound healing drugs.

It is known that β₃-adrenergic receptor agonists are capable of being used for the treatment of obesity and diabetes, although the clinical proof of this activity has not been provided with certainty.

It is also known that β₃-adrenergic receptor agonists, hereafter abbreviated to "β₃-agonists", have been proposed as intestinal spasmolytics for the treatment of gastrointestinal diseases, more particularly inflammatory bowel disease (IBD) and irritable colon syndrome, and for protection of the gastrointestinal tract from the side effects of non-steroidal anti-inflammatory drugs.

The term "β₃-agonists" includes β receptor agonist compounds which have been defined as "atypical" or "non-β₁non-β₂" and which are now recognized as a subtype of adrenergic receptor called "β₃".

The treatment of wounds which do not heal represents a serious clinical problem that is difficult to solve because the healing of wounds involves a complex series of phenomena which overlap and which are difficult to control globally.

Growth factors, especially basic Fibroblast Growth Factor (bFGF, Biol. Pharm. Bull., 1996, 19(4), 530–535) and acidic Fibroblast Growth Factor (aFGF, J. Invest. Dermatol., 1995, 104, 850–855), as well as sphingosylphosphorylcholine, J. Invest. Dermatol., 1996, 106, 232–237, have been proposed as wound healing agents.

It has now been found that β₃-agonists possess a definite activity on the healing of wounds in mammals.

More particularly, it has been found that β₃-agonists act by accelerating the healing of skin wounds in diabetic mammals.

Thus, according to one of its features, the present invention relates to the use of β₃-agonists for the preparation of pharmaceutical compositions intended for accelerating the healing of wounds.

More particularly, the invention relates to the use of β₃-agonists for the preparation of wound healing drugs.

β₃-agonists which are useful according to the present invention are represented by formula (I):

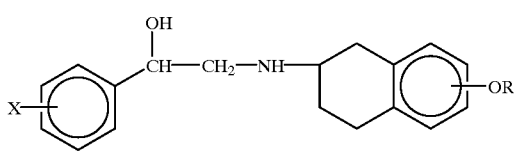

(I)

in which:

X is hydrogen, a halogen, a trifluoromethyl group or a $(C_1-C_4)$alkyl group; and R is hydrogen or a methyl group which is unsubstituted or substituted by a carboxyl or lower carbalkoxy group, and their pharmaceutically acceptable salts, indicated in EP 0 211 721 and EP 0 303 546, which describe compounds of formula (1) which are useful as intestinal spasmolytics.

Among the compounds of formula (I), the following compounds:

2-[(7-hydroxy-1,2,3,4-tetrahydronaphth-2-yl)amino]-phenylethanol;

2-[(7-hydroxy-1,2,3,4-tetrahydronaphth-2-yl)amino]-1-(3-chlorophenyl)-ethanol;

2-[(7-carbethoxymethoxy-1,2,3,4-tetrahydronaphth-2-yl)amino]-1-(3-chlorophenyl)ethanol;

2-[(7-carbethoxymethoxy-1,2,3,4tetrahydronaphth-2-yl)amino]-1-phenylethanol;

(1R,2'RS)-2-[(7-hydroxy-1,2,3,4tetrahydronaphth-2-yl)amino]-1-phenyl-ethanol;

(1S,2'RS2-[(7-hydroxy-1,2,3,4-tetrahydronaphth-2-yl)amino]-1-phenyl-ethanol;

(+)-(1R)-2-[(7-hydroxy-1,2,3,4tetrahydronaphth-2-yl)amino]-1-phenyl-ethanol;

(+)-(1S)-2-[(7-hydroxy-1,2,3,4-tetrahydronaphth-2-yl)amino]-1-phenyl-ethanol;

(−)-(1R)2-[(7-hydroxy-1,2,3,4-tetrahydronaphth-2-yl)amino]-1-phenyl-ethanol;

(−)-(1S)-2-[(7-hydroxy-1,2,3,4-tetrahydronaphth-2-yl)amino]-1-phenyl-ethanol;

N-[(2R)-7-ethoxycarbonylmethoxy-1,2,3,4-tetrahydronaphth-2-yl]-(2R)-(3-chlorophenyl)-2-hydroxyethanamine;

N-[(2R)-7-methoxycarbonylmethoxy-1,2,3,4-tetrahydronaphth-2-yl]-2R)-2-(3-chlorophenyl)-2-bydroxyethanamine;

and especially N-[(2S7ethoxycarbonylmethoxy-1,2,3,4tetrahydronaphth-2-yl]-(2R)-2-(3-chlorophenyl)-2-hydroxyethanamine (SR 58611), and their pharmaceutically acceptable salts, are particularly advantageous.

Other β₃-agonists which are useful according to the present invention are represented by formula (II):

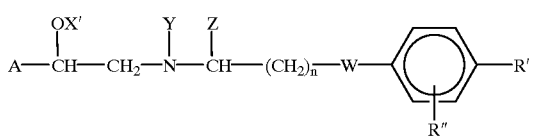

(II)

in which:

n is 1, 2 or 3;

A is a benzofuran-2-yl group or a phenyl group which is unsubstituted or substituted by one or two halogen atoms or by a $(C_1-C_4)$alkyl or trifluoromethyl group;

R' is:

a hydrogen;

a $(C_1-C_6)$alkyl group;

a functional group selected from the following groups: hydroxyl; $(C_1-C_6)$alkoxy; $(C_2-C_6)$alkenyloxy; $(C_2-C_6)$alkynyloxy; $(C_3-C_8)$cycloalkoxy; $(C_3-C_8)$-cycloalkyl $(C_1-C_6)$alkoxy; benzyloxy; phenoxy; mercapto; $(C_1-C_6)$alkylthio; $(C_2-C_6)$alkenylthio; $(C_2-C_6)$alkynylthio; $(C_3-C_8)$cycloalkylthio; $(C_3-C_8)$cycloalkyl-$(C_1-C_6)$alkylthio; benzylthio; phenylthio; $((C_1-C_6)$alkyl)sulfinyl; $((C_2-C_6)$ alkenyl)-sulfinyl; ((C₂–C₆)alkynyl)sulfonyl; (C₃–C₈) cycloalkylsulfonyl; ((C₃–C₈)cycloalkyl) (C₁–C₆)alkyl) sulfonyl; benzylsulfonyl; phenylsulfonyl; ((C₁–C₆)alkyl) sulfonyl; ((C₂–C₆)alkenyl)sulfonyl; ((C₂–C₆)alkynyl) sulfonyl; (C₃–C₈)cycloalkylsulfonyl; ((C₃–C₈)cycloalkyl (C₁–C₆)alkyl)sulfonyl; benzylsulfonyl; phenylsulfonyl; cyano; nitro; amino which is unsubstituted or substituted by one or two identical or different radicals selected from (C₁–C₆)alkyl, (C₂–C₆)alkenyl, (C₂–C₆)alkynyl, (C₃–C₈) cycloalkyl, (C₃–C₈)cycloalkyl(C₁–C₆)alkyl, benzyl, phenyl; carboxyl; carbalkoxy in which the alkyl group is C₁–C₆; ((C₂–C₆)alkenyloxy)carbonyl; ((C₂–C₆)alkynyloxy) carbonyl; (C₃–C₈)cycloalkylcarbonyl; ((C₃–C₈)cycloalkyl (C₁–C₆)alkoxy)carbonyl; benzyloxycarbonyl; phenoxycarbonyl; carbamoyl which is unsubstituted or substituted on the amino group by one or two identical or different radicals selected from (C₁–C₆)alkyl, (C₂–C₆)alkenyl, (C₂–C₆) alkynyl, (C₃–C₈)-cycloalkyl, (C₃–C₈)cycloalkyl(C₁–C₆) alkyl, benzyl and phenyl groups;

a group R''' selected from the groups: (C₁–C₆)alkyl substituted by a functional group; (C₂–C₆)alkenyl substituted by a functional group; (C₂–C₆)alkynyl substituted by a functional group; phenyl(C₁–C₆)alkyl substituted on the phenyl group by a (C₁–C₆)alkyl or by a functional group; phenyl(C₂–C₆)alkenyl substituted on the phenyl group by a (C₁–C₆)alkyl or by a functional group; phenyl(C₂–C₆) alkynyl substituted on the phenyl group by a (C₁–C₆)alkyl or by a functional group; benzyl substituted on the phenyl group by a (C₁–C₆)alkyl or by a functional group; and phenyl which is unsubstituted or substituted by a (C₁–C₆) alkyl or by a functional group, the functional group being as defined above;

a group O-R''', S-R''', SO-R''' or SO₂—R''', in which R''' is as defined above for R';

a group NR'''R°, in which R''' is as defined above and R' is hydrogen or is as defined above for R''', or R''' and R° form, together with the nitrogen to which they are bonded, a group selected from pyrrolidino, piperidino and morpholino groups;

a group COOR''' or a group CO-SR''', in which R''' is as defined above;

a group CONR'''R°, in which R''' is as defined above and R° is hydrogen or is as defined above for R''', or R''' and R° form, together with the nitrogen to which they are bonded, a group selected from pyrrolidino, piperidino and morpholino groups; or a group SO₂NR'''R°, in which R''' is as defined above and R° is hydrogen or is as defined above for R''', or R''' and R° form, together with the nitrogen to which they are bonded, a group selected from pyrrolidino, piperidino and morpholino groups;

R'' is:
a hydrogen;
a halogen;
a (C₁–C₆)alkyl group;
a functional group as defined above for R';
a group OR''', R''' being as defined above;
a group COOR''', R''' being as defined above;

a group CONR'''R°, in which R''' is defined above and R° is hydrogen or is as defined above for R''', or R''' and R° form together with the nitrogen to which they are bonded, a group selected from pyrrolidino, piperidino and morpholino groups;

W is a direct bond or an oxygen atom;

X' is hydrogen, a (C₁–C₆)alkyl or a (C₁–C₆) alkycarbonyl;

Y is hydrogen or a group A'—CH(OH)—CH₂—, A' being identical to A but other than benzofuran-2-yl; or X' and Y, taken together, form a methylene group optionally substituted by a carbalkoxy group in which the alkyl group is C₁–C₆; an ethylene group optionally substituted by an oxo group; or a 1,3-propylene group;

Z is hydrogen or a (C₁–C₆)alkyl, and their pharmaceutically acceptable salts, indicated in EP 0 255 415, which describes the use of compounds of formula (II) as intestinal spasmolytics.

Other β₃-agonists which are also useful according to the present invention are represented by formula (III):

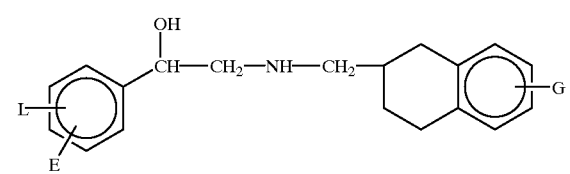

(III)

in which:

E is hydrogen, a (C₁–C₄)alkyl group, a (C₁–C₄)alkoxy group, a phenyl group, a nitro group, a halogen atom or a trifluoromethyl group;

L is hydrogen, a (C₁–C₄)alkyl group, a (C₁–C₄)alkoxy group, a phenyl group, a nitro group or a halogen atom; or E and L together are a group —CH═CH—CH—CH— or —CH₂—CH₂—CH₂—CH₂—; and G is hydrogen, a chlorine atom, a hydroxyl group or a group OG', in which G' is a (C₁–C₄)alkyl group which is unsubstituted or substituted by a hydroxyl, (C₁–C₄)alkoxy, (C₁–C₄)alkoxycarbonyl, carboxyl or (C₃–C₇)cycloalkyl group; a (C₃–C₇) cycloalkyl group; or a (C₂–C₄)alkanoyl group, and their pharmaceutically acceptable salts, indicated in EP 0436435, which describes compounds of formula (o) that are useful as intestinal spasmolytics.

Among the compounds of formula (III), N-[(6hydroxy-1,2,3,4-tetrahydro-naphthalen-(2R)-2-yl)methyl]-(2R)-2-hydroxy-2-(3-chlorophenyl)ethanamine (SR 59104), N-[(7-methoxy-1,2,3,4-tetrabydonaphthalen-(2R)-2-yl)methyl]-(2R)-2-hydroxy-2-(3-chlorophenyl)ethanamine (SR 59119) and their pharmaceutically acceptable salts are particularly advantageous compounds.

Other advantageous β₃-agonist compounds according to the present invention are:

the compound BRL 35135 described in EP 23385, of the formula

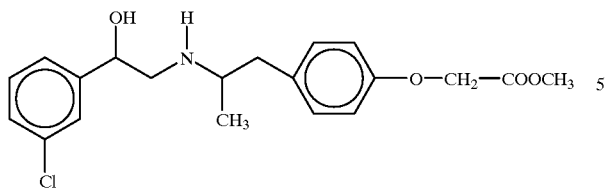
the compound CL 316243 described in U.S. Pat. No. 5,061,727, of the formula
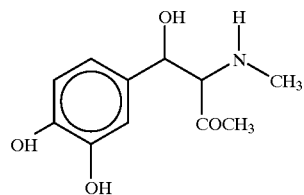
the compound BMS 187257 described in U.S. Pat. No. 5,321,036, of the formula
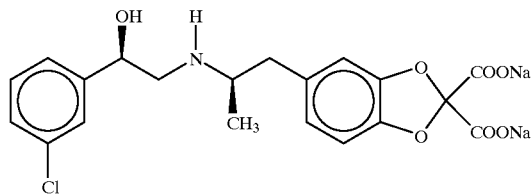
the compound AZ 002 described in EP 218440, of the formula
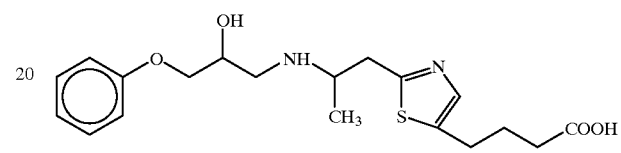
the compound L-755507 of the formula
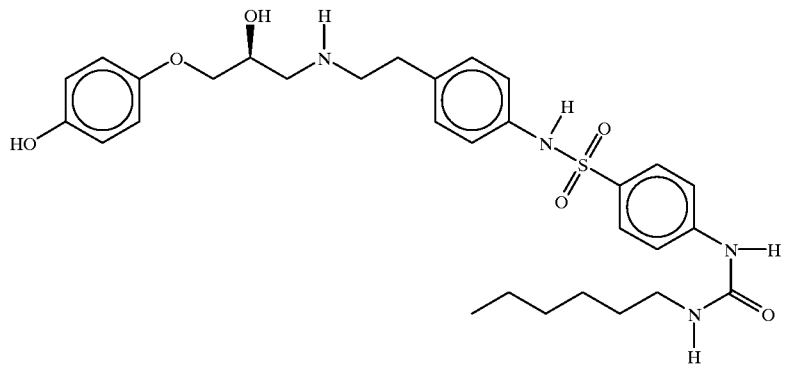
and the compound L-750355 of the formula
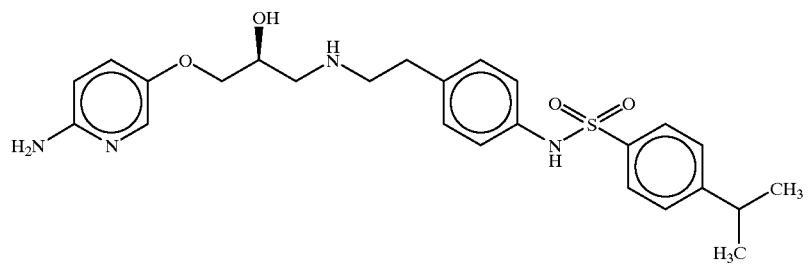
which are described in EP 611003;

the compound FR-149175 described in Japan J. Pharmacol., 1997, 74. (1): 109, of the formula

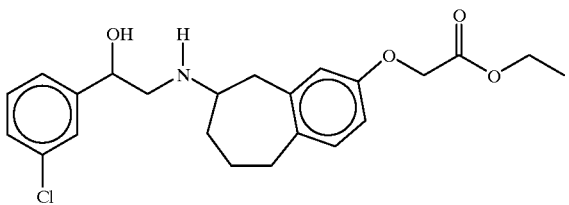

the compound SB-226552 described in Int. J. Obesity, 1997, 21, Suppl. 2: 560, of the formula

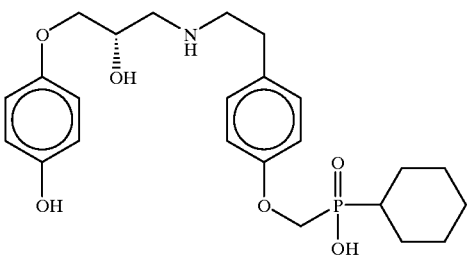

and the products described in the following patents/patent applications: WO 96/35671, WO 96/35670, WO 96/16038, WO 96104233, WO 95/33724, WO 95/29159, EP 659737, WO 95/04047, EP 516349, EP 473285, EP 23385, EP21636, EP 7205, JP08198866, JP08165276, JP08157470, WO96116938, EP 714883, WO 96/04234, U.S. Pat. No. 5,488,064, U.S. Pat. No. 5,482,971, U.S. Pat. No. 5,491,134, WO 95/29159, WO 95133724, ZA 9409874, WO 95/29903, U.S. Pat. No. 5,461,163, WO 95125104, EP 659737, JP 07112958, WO 9518527, WO 95/07284, JP 07025756, WO 95/03289, WO 95104047, WO 95/01170, WO 94/29290, U.S. Pat. No. 5,373,020, JP 06293664, WO 94/12166, EP 611003, WO 97/10825, WO 97121666, WO 97/21665, 3P 09118655, WO 97/15549, GB 2305665, EP 764640, EP 764632, WO 97/10822.

The activity of the compounds was demonstrated by means of a test for measuring the healing after a 1 cm² skin lesion had been created on the back of a mouse by removing a fragment of skin. Diabetic animals were subjected to a study of $\beta_3$-agonist versus placebo. The compound was administered orally at a rate of 10 mg/kg. The healing was evaluated by daily measurement of the surface area of the lesion in the treated animals and in those receiving the placebo.

The results of this study showed a clear difference in healing between the animals treated with the $\beta_3$-agonist compound and the animals receiving the placebo, namely that the lesions heal much more quickly for the treated animals than for those receiving the placebo.

By virtue of this particular healing activity and their low toxicity, enabling them to be used as drugs, the $\beta_3$-agonist compounds can definitely be employed in the prophylaxis and/or treatment of skin wounds, especially in the prophylaxis and/or treatment of wounds in the lower limbs of diabetic mammals.

Thus, according to another of its features, the present invention relates to a method for the prophylaxis and/or treatment of wounds in mammals, said method being characterized in that a prophylactic and/or effective amount of a $\beta_3$-agonist compound is administered to said mammals requiring said prophylaxis and/or said treatment.

More particularly, according to one preferred feature, the present invention relates to a method for the prophylaxis and/or treatment of wounds in mammals, said method being characterized in that a prophylactic and/or effective amount of a compound selected from the compounds of formulae (I), (II) and (III) is administered to said mammals requiring said prophylaxis and/or said treatment.

The amount of active principle to be administered in the treatment of wounds according to the present invention depends on the nature and severity of the complaints to be treated and on the potency of the compound and the patient's weight. The dose is generally between 0.01 and 30 mg per kg of body weight, preferably between 0.1 and 20 mg per kg of body weight and especially between 1 and 10 mg per kg of body weight.

This dose can optionally be subdivided into 2, 3 or 4 administrations throughout the day. Preferably, the active principle is formulated in dosage units containing from 0.1 to 400 mg and preferably from 0.5 to 200 mg of active principle, in combination with a pharmaceutical carrier.

In the case of local treatment, which can complement systemic administration, the dosage unit depends on the severity and extent of the wounds and on the concentration of active principle in the pharmaceutical formulation.

The normal practice is to use a cream, an ointment or a gel containing from 0.01 to 5%, advantageously from 0.025 to 2.5% and preferably from 0.1 to 1% of $\beta_3$-agonist, mixed with the customary excipients for topical application.

It is also possible to use a lotion or, in general, a solution or suspension in which the β3-agonist is present at concentrations of 0.0001 to 1%.

In the pharmaceutical compositions of the present invention for oral, sublingual, subcutaneous, intramuscular, intravenous, transdermal, rectal or local administration, the active principles can be administered to animals and humans in unit forms of administration, either as such, for example in lyophilized form, or mixed with conventional pharmaceutical carriers, for the treatment of the above-mentioned complaints. The appropriate unit forms of administration include oral forms such as tablets, which may be divisible, gelatin capsules, powders, granules and solutions or suspensions to be taken orally, sublingual and buccal forms of administration, subcutaneous, intramuscular or intravenous forms of administration, local forms of administration and rectal forms of administration.

When a solid composition is prepared in the form of tablets, the main active ingredient is mixed with a pharmaceutical vehicle such as gelatin, starch, lactose, magnesium stearate, talcum, gum arabic or the like. The tablets can be coated with sucrose or other appropriate substances, or else they can be treated so as to have a prolonged or delayed activity and so as to release a predetermined amount of active principle continuously.

A preparation in the form of gelatin capsules is obtained by mixing the active ingredient with a diluent and pouring the resulting mixture into soft or hard gelatin capsules.

A preparation in the form of a syrup or elixir can contain the active ingredient together with a sweetener, which is preferably calorie-free, methyl-paraben and propylparaben as antiseptics, a flavoring and an appropriate color.

The water-dispersible powders or granules can contain the active ingredient mixed with dispersants, wetting agents or suspending agents, such as polyvinyl-pyrrolidone, as well as with sweeteners or taste correctors.

Rectal administration is effected using suppositories, which are prepared with binders melting at the rectal temperature, for example cocoa butter or polyethylene glycols.

Parenteral administration is effected using aqueous suspensions, saline solutions or injectable sterile solutions containing pharmacologically compatible dispersants and/or wetting agents, for example propylene glycol or butylene glycol.

The active principle can also be formulated as microcapsules, optionally with one or more carriers or additives.

For local administration, the active principle is mixed with an excipient for the preparation of lotions, gels, creams or unguents, or it is dissolved in an appropriate vehicle.

In the pharmaceutical compositions according to the present invention, the active principle can also be in the form of an inclusion complex in cyclodextrins, their ethers or their esters.

What is claimed is:

1. A method for accelerating the healing of wounds in mammals comprising administering to said mammals a wound-healing accelerating amount of a $\beta_3$-agonist.

2. A method according to claim 1 for accelerating the healing of wounds in the lower limbs of diabetic mammals.

3. A method according to claim 1 wherein the $\beta$3-agonist is a compound of formula (1):

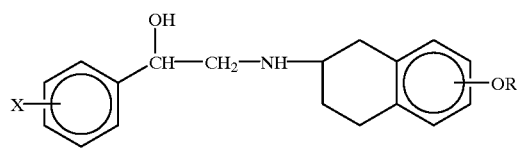

(I)

in which:

X is hydrogen, a halogen, a trifluoromethyl group or a $(C_1–C_4)$alkyl group; and R is hydrogen or a methyl group which is unsubstituted or substituted by a carboxyl or lower carbalkoxy group, or one of its pharmaceutically acceptable salts.

4. A method according to claim 3, wherein the $\beta_3$-agonist is N-[(2R)-7-ethoxycarbonylmethoxy-1,2,3,4-tetrahydronaphth-2-yl]-(2R)-2-(3-chlorophenyl)-2-hydroxyethanamine or one of its pharmaceutically acceptable salts.

5. A method according to claim 1 wherein the $\beta_3$-agonist is a compound of formula (II):

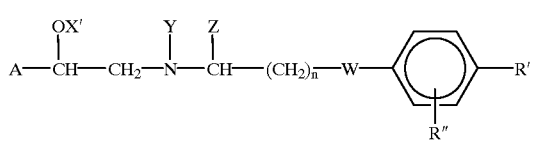

(II)

in which:

n is 1, 2 or 3;

A is a benzofuran-2-yl group or a phenyl group which is unsubstituted or substituted by one or two halogen atoms or by a $(C_1–C_4)$alkyl or trifluoromethyl group;

R' is:

a hydrogen;

a $(C_1–C_6)$alkyl group;

a functional group selected from the following groups: hydroxyl; $(C_1–C_6)$-alkoxy; $(C_2–C_6)$alkenyloxy; $(C_2–C_6)$alkynyloxy; $(C_3–C_8)$cycloalkoxy; $(C_3–C_8)$-cycloalkyl$(C_1–C_6)$alkoxy; benzyloxy, phenoxy; mercapto; $(C_1–C_6)$alkylthio; $(C_2–C_6)$alkenylthio; $(C_2–C_6)$alkynylthio; $(C_3–C_8)$cycloalkylthio; $(C_3–C_8)$cycloalkyl$(C_1–C_6)$alkylthio; benzylthio; phenylthio; $((C_1–C_6)$alkyl)sulfinyl; $((C_2–C_6)$alkenyl)sulfinyl; $((C_2–C_6)$alkynyl)sulfinyl; $(C_3–C_8)$cycloalkylsulfonyl; $((C_3–C_8)$cycloalkyl$(C_1–C_6)$alkyl)sulfinyl; benzylsulfonyl; phenylsulfonyl; $((C_1–C_6)$alkyl)sulfonyl; $((C_2–C_6)$-alkenyl)sulfonyl; $((C_2–C_6)$alkynyl)sulfonyl; $(C_3–C_8)$cycloalkylsulfonyl; $((C_3–C_8)$-cycloalkyl$(C_1–C_6)$alkyl)sulfonyl; benzylsulfonyl; phenylsulfonyl; cyano; nitro; amino which is unsubstituted or substituted by one or two identical or different radicals selected from $(C_1–C_6)$alkyl, $(C_2–C_6)$alkenyl, $(C_2–C_6)$alkynyl, $(C_3–C_8)$cycloalkyl, $(C_3–C_8)$cycloalkyl$(C_1–C_6)$alkyl, benzyl, phenyl; carboxyl; carbalkoxy in which the alkyl group is $C_1–C_6$; $((C_2–C_6)$alkenyloxy)carbonyl; $((C_2–C_6)$alkynyloxy)carbonyl; $(C_3–C_8)$cycloalkoxycarbonyl; $((C_3–C_8)$cycloalkyl$(C_1–C_6)$alkoxy)carbonyl; benzyloxy-carbonyl; phenoxycarbonyl; carbamoyl which is unsubstituted or substituted on the amino group by one or two identical or different radicals selected from $(C_1–C_6)$alkyl, $(C_2–C_6)$alkenyl, $(C_2–C6)$alkynyl, $(C_3–C_8)$cycloalkyl, $(C_3–C_8)$cycloalkyl$(C_1–C_6)$alkyl, benzyl and phenyl groups;

a group R''' selected from the groups: $(C_1–C_6)$alkyl substituted by a functional group; $(C_2–C_6)$alkenyl substituted by a functional group; $(C_2–C_6)$alkynyl substituted by a functional group; phenyl$(C_1–C_6)$alkyl substituted on the phenyl group by a $(C_1–C_6)$alkyl or by a functional group; phenyl$(C_2–C_6)$alkenyl substituted on the phenyl group by a $(C_1–C_6)$alkyl or by a functional group; phenyl$(C_2–C_6)$alkynyl substituted on the phenyl group by a $(C_1–C_6)$alkyl or by a functional group; benzyl substituted by a $(C_1–C_6)$alkyl or by a functional group; and phenyl which is unsubstituted or substituted by a $(C_1–C_6)$alkyl or by a functional group, the functional group being as defined above for R';

a group O-R''', S-R''', SO-R''' or SO$_2$R''', in which R''' is as defined above;

a group NR'''R°, in which R''' is as defined above and R° is hydrogen or is as defined above for R''', or R''' and R° form, together with the nitrogen to which they are bonded, a group selected from pyrrolidino, piperidino and morpholino groups;

a group COOR''' or a group COSR''', in which R''' is as defined above;

a group CONR'''R°, in which R''' is as defined above and R° is hydrogen or is as defined above for R''', or R''' and R° form, together with the nitrogen to which they are bonded, a group selected from pyrrolidino, piperidino and morpholino groups; or a group SO$_2$NR'''R°, in which R''' is as defined above and R° is hydrogen or is as defined above for R''', or R''' and R° form, together with the nitrogen to which they are bonded, a group selected from pyrrolidino, piperidino and morpholino groups;

R'' is:

a hydrogen;

a halogen;

a $(C_1–C_6)$alkyl group;

a functional group as defined above for R';

a group OR''', R''' being as defined above;

a group COR''', R''' being as defined above; or a group CONR'''R°, in which R''' is as defined above and R° is hydrogen or is as defined above for R''', or R''' and R° form, together with the nitrogen to which they are bonded, a group selected from pyrrolidino, piperidino and morpholino groups;

W is a direct bond or an oxygen atom;

X' is hydrogen, a ($C_1$–$C_6$)alkyl or a ($C_1$–$C_6$)alkylcarbonyl;

Y is hydrogen or a group A'—CH(OH)$CH_2$—, A' being identical to A but other than benzofuran-2-yl; or X' and Y, taken together, form a methylene group optionally substituted by a carbalkoxy group in which the alkyl group is $C_1$–$C_6$; an ethylene group optionally substituted by an oxo group; or a 1,3-propylene group;

Z is hydrogen or a ($C_1$–$C_6$)alkyl, or one of its pharmaceutically acceptable salts.

6. A method according to claim 1 wherein the $\beta_3$-agonist is a compound of formula (III):

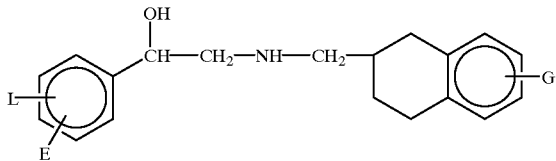

(III)

in which:

E is hydrogen, a ($C_1$–$C_4$)alkyl group, a ($C_1$–$C_4$)alkoxy group, a phenyl group, a nitro group, a halogen atom or a trifluoromethyl group;

L is hydrogen, a ($C_1$–$C_4$)alkyl group, a ($C_1$–$C_4$)alkoxy group, a phenyl group, a nitro group or a halogen atom; or E and L together are a group —CH=CH—CH=CH— or —$CH_2$—$CH_2$—$CH_2$—$CH_2$—; and G is hydrogen, a chlorine atom, a hydroxyl group or a group OG', in which G' is a ($C_1$–$C_4$)alkyl group which is unsubstituted or substituted by a hydroxyl, ($C_1$–$C_4$)alkoxy, ($C_1$–$C_4$)alkoxycarbonyl, carboxyl or ($C_3$–$C_7$)cycloalkyl group; a ($C_3$–$C_7$)cycloalkyl group; or a ($C_2$-C)alkanoyl group, or one of its pharmaceutically acceptable salts.

7. A method according to claim 6, wherein the $\beta_3$-agonist is selected from N-[(6-hydroxy-1,2,3,4-tetrahydronaphthalen-(2R)-2-yl)methyl]-(2R)-2-hydroxy-2-(3-chlorophenyl)ethanamine, N-[(7-methoxy-1,2,3,4-tetrahydronaphthalen-(2R2-yl)methyl]-(2R)-2-hydroxy-2-(3-chlorophenyl)ethanamine and their pharmaceutically acceptable salts.

8. A method for the prophylaxis or treatment of wounds in mammals which comprises administering to mammals in need of such treatment an effective amount of a $\beta_3$-agonist.

* * * * *